United States Patent [19]

Schulman

[11] 4,440,169

[45] Apr. 3, 1984

[54] OPHTHALMIC SURGICAL INSTRUMENT

[76] Inventor: Melvin L. Schulman, #B1 Cornwall Ct. (Off Cranbury Rd.), East Brunswick, N.J. 08816

[21] Appl. No.: 371,552

[22] Filed: Apr. 26, 1982

[51] Int. Cl.³ .............................................. A61B 17/32
[52] U.S. Cl. ...................................... 128/305; 30/241
[58] Field of Search ....................... 128/305, 310, 347; 30/241, 242

[56] References Cited

U.S. PATENT DOCUMENTS

| | | | |
|---|---|---|---|
| 3,895,636 | 7/1975 | Schmidt | 128/305 |
| 3,989,033 | 11/1976 | Halpern et al. | 128/305 |
| 4,018,228 | 4/1977 | Goosen | 128/305 |
| 4,368,734 | 1/1983 | Banko | 128/305 |

Primary Examiner—John D. Yasko
Attorney, Agent, or Firm—Arthur L. Plevy

[57] ABSTRACT

A surgical instrument for performing a peripheral iridectomy includes a housing having a needle portion and an internal hollow. Located within the housing are grasping means which can be moved by the surgeon to grasp the tissue of the iris and to be withdrawn so that the tissue is pulled through the aperture in the needle portion into the hollow of the housing. The tissue of the iris when pulled into the housing is directed through an aperture existing between a cutter mechanism. The cutter mechanism is then activated by the surgeon to cut a predetermined amount of tissue to thereby complete the iridectomy. The tissue cut remains in the housing.

10 Claims, 7 Drawing Figures

OPHTHALMIC SURGICAL INSTRUMENT

BACKGROUND OF INVENTION

There are many types and designs of instruments which have been developed and used in ophthalmic surgery. Such devices may be inserted into the eye and used to perform cutting or surgical procedures.

An example of such a device is depicted in U.S. Pat. No. 3,945,375 entitled Rotatable Surgical Instrument which issued on Mar. 23, 1976 to A. Banko. In this instrument, the cutting member operates like a drill bit. Tissue is drawn inside as the cutter rotates.

Other patents such as U.S. Pat. No. 4,061,146 entitled Tissue Macerating Instrument issued on Dec. 6, 1967 to E. F. Baehr, et al. This patent shows a tool used in a cataract operation. The instrument employs a rotating cutter which is again inserted into the eye to perform cataract surgery.

Other patents such as U.S. Pat. No. 4,167,943, U.S. Pat. No. 4,200,106 and U.S. Pat. No. 4,236,519 depict various devices for performing eye surgery. These devices relate to cutters and other instruments as punches for operating on or in association with the cornea or other parts of the eye.

As indicated above, such instruments are extremely useful to the surgeon and for example, they have substantially reduced the operating time and therefore provide for faster patient recovery.

In any event, there is a fairly common operation which is performed known as a peripheral iridectomy. In such an operation, an aperture or hole is made by the surgeon in the iris of the eye. This hole is made to alleviate pressure and to further be used in cataract procedures. Essentially, the irridectomy is a fairly common operation and is performed many times during the course of a year in this country and elsewhere. The operation as presently performed requires that the surgeon cut through the cornea of the eye to gain access to the iris and thereafter cut a hole or remove a portion of the iris, thus completing the iridectomy. As one can ascertain, the cutting of the eye, as well as the attendant surgery is relatively complicated and time consuming and further involves a fairly extensive recovery period for the patient.

It is therefore an object of the present invention to provide a surgical instrument which can be employed by the surgeon to perform an iridectomy in a simple procedure thus eliminating many of the disadvantages as present in the prior art.

DETAILED DESCRIPTION OF THE PREFERRED EMBODIMENT

A surgical instrument particularly adaptable for performing a peripheral iridectomy comprising a hollow tubular member having a pointed end portion with a front opening in said pointed end portion, movable tissue grasping means located in the hollow of said tubular member and operative when moved in a first direction to pass through said opening to grasp tissue and when moved in a second direction to draw said grasped tissue through said opening into said hollow of said tubular member, and cutting means located in the hollow of said tubular member and operative to cut said tissue as drawn into said hollow.

DETAILED DESCRIPTION OF THE INVENTION

Figure 1:
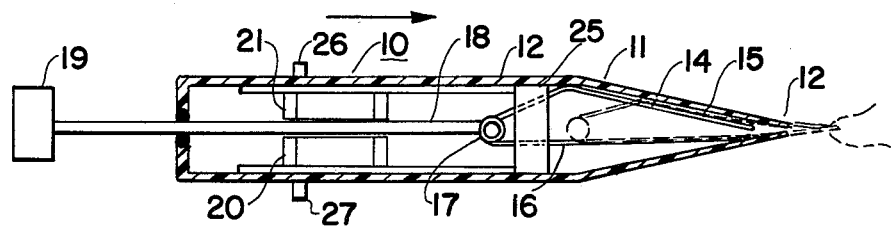
FIG. 1 is a side elevational view of a surgical instrument according to this invention.

Referring to FIG. 1, the instrument 10 includes a front portion 11 which is a tapered needle type projection capable of penetrating and being inserted into the tissue of the eye. The needle portion 11 is contiguous with the body portion 12 which may be a cylindrical or other configuration.

Figure 2:
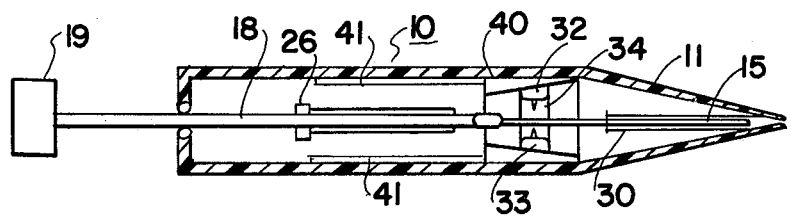
FIG. 2 is a top plan view partially in cross-section of the surgical instrument.
Figure 3:
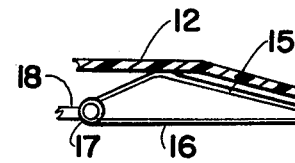
FIG. 3 is a side plan view of a grasping mechanism used in this invention.

FIG. 2 depicts a top view of the instrument 10 shown in FIG. 1. The entire body including the needle portion 11 and the cylindrical body portion 12 may be integrally formed from glass, steel or a suitable plastic. Essentially, the instrument 10 has an internal hollow. The needle or tip has an opening 12 which may be about 1 to 2 mm in diameter. Located within the housing is a tine like grasping mechanism 14. The mechanism 14 consists of a first tine 15 integrally formed with a second tine 16, as more clearly shown in FIG. 3. The tine 15 is of an arcuate configuration having a top apex which abuts against the inside wall of the inner housing 12. The tines 15 and 16 are prong like members fabricated from a spring steel or other spring like material and act as grasping prongs. The tine 16 is relatively flat or horizontal. Both tines 15 and 16 may be integrally formed from a single strand of spring steel or another material which has spring like capabilities. A loop of material 17 is formed between the tines 15 and 16 to enhance the spring like characteristics of the structure.

As will be explained, the tines 15 and 16 act as a grasping instrument whose operation is much like that of a forceps. Coupled to the loop 17 is a shaft 18 which is directed through the body 12 and terminates outside the body in a plunger 19. The shaft is supported concentric with the body 12 by means of suitable supporting ribs as 20 and 21. Mechanisms for supporting shafts within cylindrical members are well-known.

As seen from FIG. 1 and as will be further explained, located adjacent the needle portion 11 and within the hollow of the housing is a cutting mechanism 25. The cutting mechanism 25 consists of two cutter blades which are operated by the surgeon pushing two prongs as 26 and 27, which prongs are located within a slot on either side of the housing. As will be explained, a surgeon, by pushing the prongs forward can activate the cutter.

As seen in FIG. 2, located above the tine 15 is a slot 30. The slot 30 is directed towards the tip of the needle and is an extremely narrow slot but of a width sufficient to allow the tine 15 to spring upwardly as the plunger 19 is pushed by the surgeon, as will be explained.

Shown in FIG. 2, is a top view of the cutter mechanism 25. The view in FIG. 2 is in a partial section for a complete understanding. The cutter 25 includes two cutting blades 32 and 33 which are positioned in a slot or groove 34 located about periphery of the housing.

Figure 4:
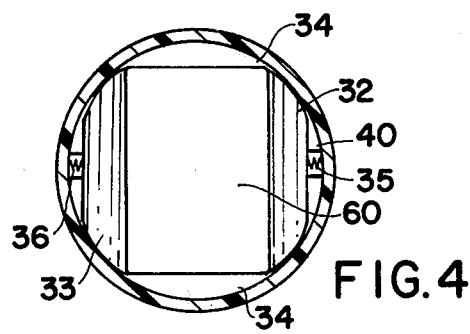
FIG. 4 is a front view of a cutter mechanism.

As seen in FIG. 4, the blades or cutters 32 and 33 are planar members and are fabricated from a steel or other material and are extremely sharp. The blades are positioned in grooves as 34 and are spring biased by means of springs 35 and 36 which are coupled to the inner walls of the housing through a slot 37 located in a cylindrical tapered push member 40 which is further shown in FIGS. 5 and 6.

The member 40 as also shown in FIG. 2, has an internal taper which abuts against the outer edges of the cutter blades 32 and 33. The member 40 is contiguous with an inner cylindrical member 41 which is secured to the tabs 26 and 27. A greater understanding of the operation of the device will now be had by describing the surgical procedure.

Figure 7:
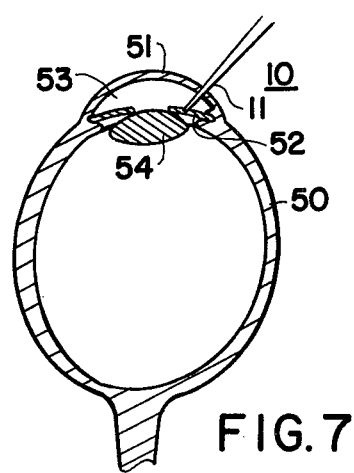
FIG. 7 is a cross-sectional view of an eye useful in explaning the iridectomy procedure.

Referring to FIG. 7, there is shown a cross-section of a typical eye 50. The structure of the eye is very well-known and reference is made to Gray's Anatomy by Crown Publishers, Inc. (1977). The eye has a front clear portion 51, known as the cornea. The iris of the eye 52 is located behind the cornea and separated from the cornea by the anterior chamber 53. The lense 54 is positioned behind the iris.

Figure 5:
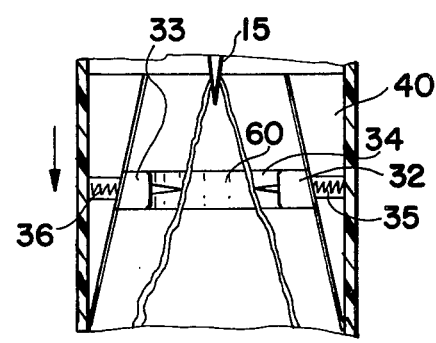
FIG. 5 is a top view of the cutter mechanism.
Figure 6:
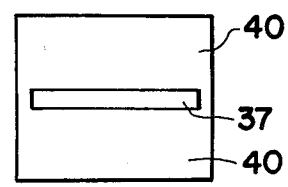
FIG. 6 is a side view of an actuator used for operating the cutter mechanism.

In using the instrument to perform an iridectomy the needle portion of the instrument is inserted through the cornea into the region of the iris. The surgeon of course has the use of an optical microscope and other devices which allows him to implace the needle portion in the exact position. When the needle portion is properly positioned with respect to the iris, the surgeon then depresses plunger 19 which moves the shaft 18 of FIG. 1 in the direction of the arrow. As soon as the apex of the upper tine 15 underlies the slot 30, the upper tine springs upwardly as shown in the dashed configuration of FIG. 1. The surgeon then positions the tines so that they overlie a portion of the tissue of the iris. The plunger is now moved by the surgeon in the opposite direction. Accordingly, as the tines are moved back into the housing; the tissue of the iris is grasped by the tines and pulled into the aperture 12 of the needle. As the surgeon continues to pull the tissue via the tines, the tissue enters the aperture 60 which is formed between the cutting blades 32 and 33. This is shown in FIG. 5. The surgeon then pulls a given amount of tissue through the aperture 60 so that the tissue of the iris is located between the blades 32 and 33. When the correct amount of tissue is present, the surgeon then pushes the projections 26 and 27 which causes the tapered member 40 to push the blades 33 and 34 into the tissue to thereby cut the same. The cut tissue remains inside the housing. The tissue of the iris which was not cut will spring back through the aperture of the needle into position. It is noted that the tissue of the iris is extremely flexible and pliable and essentially has good elasticity.

From the above description it is now clear that the iridectomy can be performed by the surgeon utilizing the simple structure depicted above. The mechanism described has the grasping and cutting means located within the instrument and hence the entire operation can be performed through the relatively small aperture which is formed in the eye during needle insertion. It is of course understood that there are alternative ways of creating a grasping mechanism, as well as a cutting mechanism which will operate to perform the surgical procedure. All such modifications and alterations are deemed to be encompassed within the spirit and scope as set forth in the claims appended hereto.

I claim:

1. A surgical instrument particularly adaptable for performing a peripheral iridectomy comprising:
    a hollow tubular member having a pointed end portion adapted to pierce solid tissue with a front opening in said pointed end portion,
    movable tissue grasping means located in the hollow of said tubular member and operative when moved in a first direction to pass through said opening to grasp tissue and when moved in a second direction to draw said grasped tissue through said opening into said hollow of said tubular member, and cutting means located in the hollow of said tubular member and selectively operative to cut said tissue as drawn into said hollow, with said cutting means when selectively operated capable of forming an aperture in said tissue of a diameter according to the distance moved by said tissue grasping means in said second direction, with said cut tissue remaining in said hollow.

2. The surgical instrument according to claim 1, wherein said movable tissue grasping means comprises a first arcuate tine having an apex directed against the inner sidewall of said tubular member, a second tine integral formed with said first tine and in the same direction, with said tine forming a spring like assembly which opens when passed through said front opening.

3. The surgical instrument according to claim 2, wherein said pointed end portion of said tubular member has a slot extending from said front opening along a length of said pointed portion and located above said first tine to allow said first tine to protrude from said slot when said grasping means is moved in said first direction.

4. The surgical instrument according to claim 1, wherein said cutting means includes at least one blade member located in said housing and means coupled to said blade member to move the same to cut tissue as located within the hollow of said housing.

5. The surgical instrument according to claim 5, wherein said means coupled to said blade member includes a movable element abutting against said blade member and operative when moved to move said blade member in a direction to cut tissue.

6. The surgical instrument according to claim 5, further including spring biasing means coupled to said blade member to allow said member to move back when said tapered member is moved from said cutting position.

7. A surgical instrument for performing a peripheral iridectomy comprising:
    a tubular hollow body having a hollow pointed piercing portion with a front opening, said pointed portion having a slot directed along a length thereof from said pointed portion,
    a grasping member comprising first and second extending tines, with a top one of said tines located below said slot, said grasping member movably positioned in said hollow body and operative when moved in a first direction towards said opening to cause said top one of said tines to spring upwardly through said slot, and operative when moved in an opposite direction to move towards said bottom tine, actuatable cutting means located in said hollow body and positioned to allow said grasping member to move past said cutting means, and means coupled to said cutting means to actuate the same.

8. The surgical instrument according to claim 7, further including a movable shaft directed along the main axis of the body of said tubular member and coupled to said grasping means to move the same in said first and second directions.

9. The surgical instrument according to claim 7, wherein said actuatable cutting means comprises first and second planar cutting blades located in the same plane and positioned apart from one another to provide a space therebetween through which said grasping means can move and actuating means coupled to said blades to move the same within said space to cut any tissue present in said space.

10. A method of performing a peripheral iridectomy, compring the steps of:
  inserting a hollow needle having a front opening through the cornea of the eye into the vicinity of the iris,
  moving a grasping member through said front opening of said needle to grasp the tissue of the iris,
  with drawing the grasped tissue through said opening into the hollow of said needle, and
  cutting the grasped tissue in said hollow.

* * * * *